(12) United States Patent
Feng et al.

(10) Patent No.: US 10,464,899 B2
(45) Date of Patent: Nov. 5, 2019

(54) ASYMMETRICALLY CATALYZED SYNTHESIS METHOD OF NITROPYRAZOLE AMIDE COMPOUND

(71) Applicant: Zhejiang Jiuzhou Pharmaceutical Co., Ltd., Taizhou (CN)

(72) Inventors: Xiaoming Feng, Taizhou (CN); Qian Yao, Taizhou (CN); Xiaohua Liu, Taizhou (CN); Lili Lin, Taizhou (CN); Yuheng Zhang, Taizhou (CN)

( * ) Notice: Subject to any disclaimer, the term of this patent is extended or adjusted under 35 U.S.C. 154(b) by 72 days.

(21) Appl. No.: 15/511,243

(22) PCT Filed: Jun. 12, 2015

(86) PCT No.: PCT/CN2015/081341
§ 371 (c)(1),
(2) Date: Aug. 1, 2017

(87) PCT Pub. No.: WO2016/045415
PCT Pub. Date: Mar. 31, 2016

(65) Prior Publication Data
US 2017/0291876 A1    Oct. 12, 2017

(30) Foreign Application Priority Data

Sep. 22, 2014   (CN) .......................... 2014 1 0486209
Feb. 12, 2015   (CN) .......................... 2015 1 0075076

(51) Int. Cl.
| | | |
|---|---|---|
| C07D 211/88 | (2006.01) |
| C07D 231/12 | (2006.01) |
| C07D 231/16 | (2006.01) |
| C07D 207/267 | (2006.01) |
| C07D 405/06 | (2006.01) |
| C07D 409/06 | (2006.01) |
| C07C 201/12 | (2006.01) |
| C07C 205/53 | (2006.01) |

(52) U.S. Cl.
CPC .......... *C07D 211/88* (2013.01); *C07C 201/12* (2013.01); *C07C 205/53* (2013.01); *C07D 207/267* (2013.01); *C07D 231/12* (2013.01); *C07D 231/16* (2013.01); *C07D 405/06* (2013.01); *C07D 409/06* (2013.01)

(58) Field of Classification Search
None
See application file for complete search history.

(56) References Cited

FOREIGN PATENT DOCUMENTS

CN       102531815 A     7/2012

OTHER PUBLICATIONS

English abstract; Chinese Application with Publication No. CN102531815A.
Tetrahedron Letters vol. 49, No. 35, Jun. 14, 2008, p. 5220.

*Primary Examiner* — Samantha L Shterengarts

(57) ABSTRACT

A synthesis method of γ-nitropyrazole amide compound through asymmetrical catalyzing technique is provided, a nitroalkane and an α,β-unsaturated pyrazole amide are applied as the raw material, a complex formed by a chiral amine oxide with a rare earth metal compound is served as the catalyst, a 4 Å molecular sieve is served as an additive, the γ-nitropyrazole amide compound can be obtained with a yield more than 99% and enantiomeric excess more than 99% ee. The catalytic system not only has the advantages of simple operation, mild reaction conditions, requiring no acid/base additives, convenient product purification, high yield and enatioselectivity, compliance with green atomic economy, and promising prospects for industrial application, but also allows the obtained γ-nitropyrazole amide compound to undergo some simple chemical conversions to produce some molecules having physiological activities.

15 Claims, No Drawings

ASYMMETRICALLY CATALYZED SYNTHESIS METHOD OF NITROPYRAZOLE AMIDE COMPOUND

This application claims one priority of Chinese Patent Application No. 201410486209.3, filed to Chinese Patent Office on Sep. 22, 2014, titled "asymmetrically catalyzed synthesis method of γ-nitropyrazole amide compound" and the other priority of Chinese Patent Application No. 201510075076.5, filed to Chinese Patent Office on Feb. 12, 2015, titled "asymmetrically catalyzed synthesis method of γ-nitropyrazole amide compound", the entire contents of which are hereby incorporated by reference.

FIELD OF INVENTION

The present invention relates to a method for synthesizing γ-nitropyrazole amide compound through asymmetrical Michael addition reaction of an α,β-unsaturated pyrazole amide with a nitroalkane in the catalytic of a complex formed by a chiral amine oxide with a rare earth metal.

BACKGROUND OF THE INVENTION

γ-nitropyrazole amide compound plays an important role in organic synthesis. It can not only be simply and highly efficiently esterified with methanol in the presence of a base, but also be simply chemically converted into biologically active compounds such as γ-amino acids, 2-pyridone and 2-pyrrolidone. Some reports referring to the asymmetrically catalyzed synthesis of γ-nitropyrazole amide are available at present.

Carlos F. Barbas III et al accomplish the asymmetric Michael addition below of pyrazole amide with a nitroalkene at −20° C. by using the thiourea derivative XIV as a chiral catalyst and chloroform as a solvent, in which the product has a yield of 34%-99%, a d.r value of 10:1→20:1 (d.r: diastereoselectivity of compounds containing two or more chiral centers), and 78%-97% ee (Angew. Chem. Int. Ed. 2012, 51, 5381).

Long Lu et al accomplish the asymmetric Michael addition below of pyrazole amide substituted with trifluoromethyl with a nitroalkane at room temperature by using the thiourea derivative 2d as a chiral catalyst and toluene as a solvent, in which the product has a yield of 71%-91%, a d.r value of 4.4:1-9.9:1 (d.r: diastereoselectivity of compounds containing two or more chiral centers), and 80%-93% ee (ACS Catal. 2013, 3, 502).

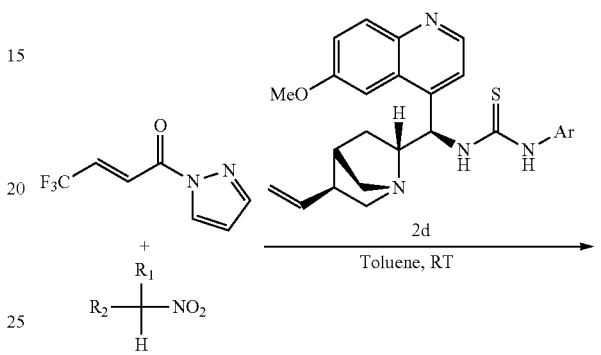

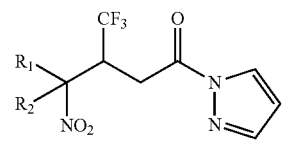

Shuji Kanemasa et al accomplish the asymmetric Michael addition of an unsaturated pyrazole amide with nitromethane at −20° C. to room temperature by using R, R-DBFOX/Ph*Ni(ClO$_4$)$_2$*3H$_2$O (A) and 2,2,6,6-tetramethylpiperidine (TMP) as a combined catalyst, and a mixture of nitromethane and tetrahydrofuran (v/v=1/1) as a solvent, in which the product has a yield of 39%-97%, and 77%-97% ee (J. Am. Chem. Soc. 2002, 124, 13394).

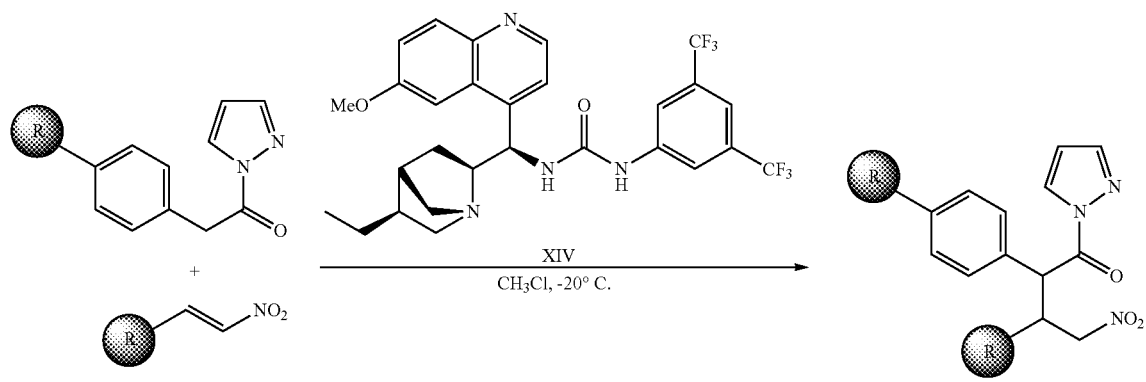

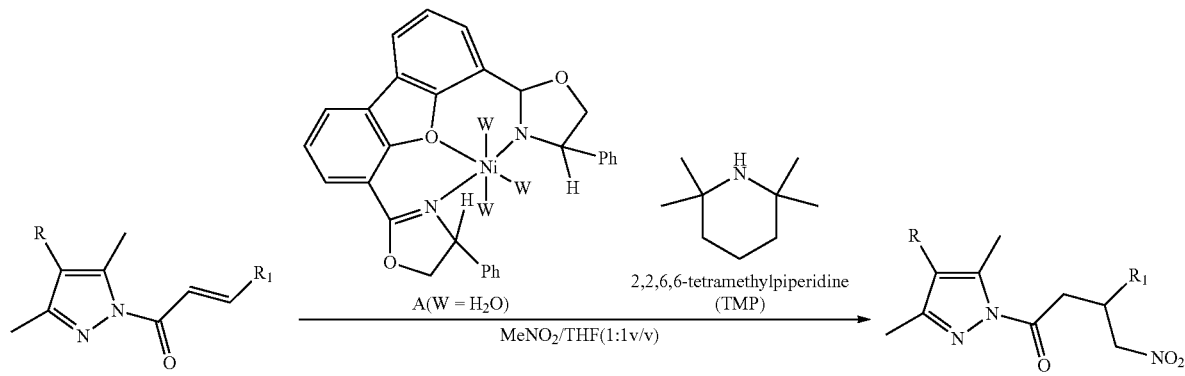

In summary, in the catalytic reaction system of Carlos F. Barbas III, the reaction needs to be carried out at −20° C., thus consuming a lot of energy. In the catalytic reaction system of Long Lu, there is a great limitation since the substrates which extending from α,β-unsaturated amides are the substrates which all substituted with trifluoromethyl at the end position. In the catalytic reaction system of Shuji Kanemasa, a step of activation at the temperature of −78° C. is needed before the start of reaction; and among the extended substrates, 11 substrates needed to be reacted at −20° C., 3 substrates needed to be reacted at 0° C., and only 2 substrates can be reacted at room temperature; the reaction time of 11 substrates is 96 hrs, and the reaction time of 6 substrates is 168 hrs; and the yield is undesirable. After the reaction, the product needed to be washed with saturated ammonium chloride and then separated and purified by column chromatography. The reaction conditions are harsh, the operation is complex, and a large amount of nitromethane is consumed (9.1 mmol nitromethane is needed per 0.1 mmol α,β-unsaturated pyrazole amide compound). Most importantly, the outcome of the reaction is undesirable. Therefore, there is an urgent need for developing an efficient, simple, energy-saving, and environmentally friendly method.

SUMMARY OF THE INVENTION

An objective of the present invention is to provide a method for synthesizing a γ-nitropyrazole amide compound through the technique of asymmetrically catalyzed Michael addition of an α,β-unsaturated pyrazole amide compound with a nitroalkane, which is efficient, simple in operation, energy saving, and environmentally friendly.

A technical solution of the present invention is as follows:

An asymmetrically catalyzed synthesis method of a γ-nitropyrazole amide compound, wherein, in the reaction that a nitroalkane and an α,β-unsaturated pyrazole amide are employed as raw materials, a complex formed by a chiral amine oxide with a rare earth metal compound is served as a catalyst, a 4 Å molecular sieve is served as an additive, after the reaction finished, to obtain a γ-nitropyrazole amide compound.

The structure of the nitroalkane is $RCH_2NO_2$, in which R=H, $CH_3$, Et, or Bn.

The structure of the α,β-unsaturated pyrazole amide compound is

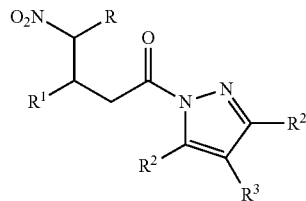

in which $R^1$=$C_6H_5$, 4-$FC_6H_4$, 4-$ClC_6H_4$, 4-$BrC_6H_4$, 4-$MeC_6H_4$, 4-$MeOC_6H_4$, 3-$BrC_6H_4$, 3-$MeC_6H_4$, 2-$BrC_6H_4$, 2-$MeOC_6H_4$, 3,4-$Cl_2C_6H_3$, 3,4-$(MeO)_2C_6H_3$, 2-Furyl, 2-Thienyl, $CH_3$, Pr, Pent, $^tBu$, EtO, EtOOC; and $R^2$=$CH_3$, Ph; $R^3$=H, Cl, Br, I;

The γ-nitropyrazole amide compound has a structure of:

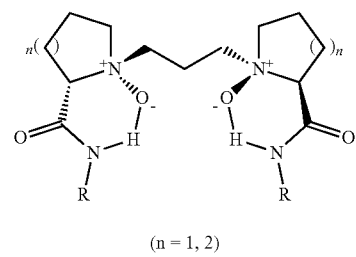

in which R, $R^1$, $R^2$, and $R^3$ are as defined above.
The structure of the chiral amine oxide ligand is

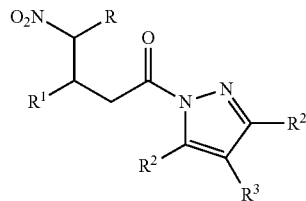

(n = 1, 2)

in which n=1 or 2; R=Ph-, 2,6-$Me_2C_6H_3$—, 2,6-$Et_2C_6H_3$—, 2,6-$iPr_2C_6H_3$—, or $Ph_2CH$—.

The reaction takes place in a solvent selected from the group consisting of alkanes, for example, pentane, hexane, heptane, and the like; haloalkanes, for example, dichloroethane, chloroform, and the like; aromatic hydrocarbons, for example, toluene, ethylbenzene, and cumene; ethers, for example, tetrahydrofuran, methyl tert-butyl ether, 2-methyltetrahydrofuran, and the like; and esters, for example, ethyl acetate, isopropyl acetate, and the like.

Preferably, the reaction temperature is 25-50° C.

Preferably, the technical solution of the present invention is as follows:

An asymmetrically catalyzed synthesis method of a γ-nitropyrazole amide compound, wherein, a nitroalkane and an α,β-unsaturated pyrazole amide are employed as raw materials, a complex formed by a chiral amine oxide with a rare earth metal compound is served as a catalyst, a 4 Å molecular sieve is served as an additive, after the reaction of 12-120 hrs in the solvent of dichloromethane at the temperature of 25-50° C. under the normal pressure, to obtain a chiral γ-nitropyrazole amide compound.

In the preparation method of the present invention, the reaction endpoint is detected by TLC, and the chiral γ-nitropyrazole amide compound is separated by silica gel column chromatography.

The rare earth metal compound is gadolinium trifluoromethanesulfonate [Gd(OTf)$_3$], scandium trifluoromethanesulfonate [Sc(OTf)$_3$], holmium trifluoromethanesulfonate [Ho(OTf)$_3$], ytterbium trifluoromethanesulfonate [Yb(OTf)$_3$], erbium trifluoromethanesulfonate [Er(OTf)$_3$], or yttrium trifluoromethanesulfonate [Y(OTf)$_3$].

The molar ratio of the nitroalkane to the α,β-unsaturated pyrazole amide compound is 1.86:1-55.8:1, and most preferably 9.3:1.

The most preferred catalyst in the reaction is a complex formed by a chiral amine oxide L6 (in which n=2, and R=2,6-iPr$_2$C$_6$H$_3$—) with gadolinium trifluoromethanesulfonate [Gd(OTf)$_3$], and the molar ratio of the chiral amine oxide to the rare earth metal compound is 0.8:1.0-1.5:1.0, and most preferably 1.2:1.0;

The 4 Å molecular sieve is activated at 450° C. for 3 hrs, and the corresponding amount of the 4 Å molecular sieve is 10-100 mg per 0.1 mmol of the α,β-unsaturated pyrazole amide.

The dichloromethane is dried by refluxing with GaH$_2$, and the amount corresponding to 0.1 mmol of the α,β-unsaturated pyrazole amide is 6.2 mmol;

The reaction temperature is 30° C.;

The reaction time is 72-96 hrs.

Further, the γ-nitropyrazole amide compound prepared through the above method is reacted with methanol in the presence of an organic base, to obtain an esterified product.

The esterified product has a structure of:

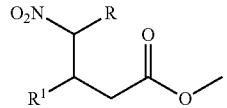

in which R and R$^1$ are as defined above.

The organic base is selected from the group consisting of triethylamine, diisoproylethylamine, trimethylamine, tri-n-propylainine, tri-n-butylamine, dimethylaniline, diethylaniline, dimethylbenzylamine, diethylbenzylamine, 1,8-azacyclo[5,4,0]undecene-7 (DBU).

Compared with the prior art, the present invention has the following notable advantages.

1. The operation is simple, the catalyst does not need to be activated, and the product can be easily separated from the catalyst, the additive, and the raw material.

2. The conversion rate and the enantioselectivity of the reaction are good, the yield is more than 99%, and the enantioselectivity is more than 99% ee.

3. The reaction system is simple and clean, and no acid/base additives are needed.

4. The reaction conditions are mild, and the reaction can take place at 30° C. under normal pressure.

5. Less nitroalkane is used, so the raw material is saved.

DETAILED EMBODIMENTS

Example 1: Michael Addition of α,β-Unsaturated pyrazole amide Compound with nitroalkane Compound, Being Catalyzed by a Complex Formed by a chiral amine oxide with Rare Earth Metal A rare earth metal compound (Nos. 1-11: 0.01 mmol, and Nos. 12-16: 0.0075 mmol), a chiral amine oxide ligand (Nos. 1-11: 0.012 mmol, and Nos. 12-16: 0.009 mmol), the α,β-unsaturated pyrazole amide 1a (0.1 mmol), a 4 Å molecular sieve (30 mg), and a stirrer were added to a reaction vessel. The reaction vessel was purged 3 times with nitrogen, and then dichloromethane (6.2 mmol) and nitromethane (Nos. 1-11: 5.6 mmol, and Nos. 12-16: 0.93 mmol) were added and stirred at 25-50° C. for 12-120 hrs. The reaction was detected by TLC. The product was purified by column chromatography, and the enantiomeric excess of the product was determined by HPLC (Daicel chiralcel IE, $V_{n\text{-}hexane}:V_{isopropanol}$=90:10, flow rate: 1.0 mL/min). The result is shown in Table 1. The reaction formula and the structure of the chiral amine oxide ligand are shown as below:

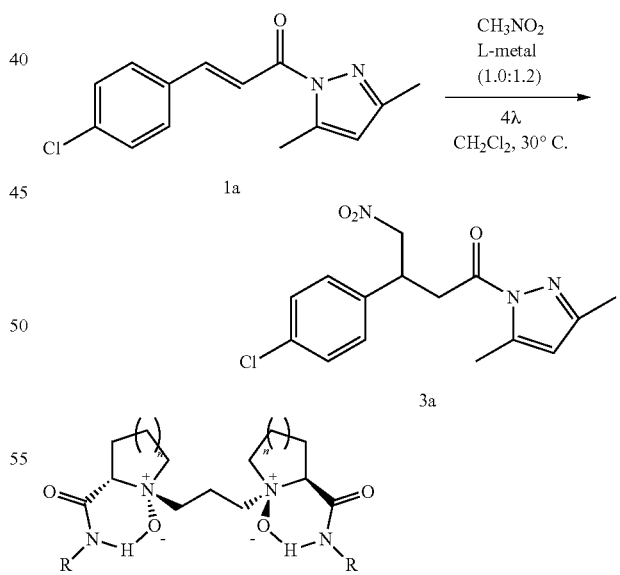

1.1 R - phenyl, n - 1
1.2 R - diphenylmethyl, n - 1
1.3 R - 2,6-dimethylphenyl, n - 1
1.4 R - 2,6-diethyphenyl, n - 1
1.5 R - 2,6-diisopropylphenyl, n - 1
1.6 R - 2,6-diisopropylphenyl, n - 2

TABLE 1

Optimized reaction conditions in asymmetric Michael addition of α,β-unsaturated pyrazole amide compound with nitroalkane compound, being catalyzed by a complex formed by a chiral amine oxide with rare earth metal

| No | Chiral amine oxide ligand | Rare earth metal compound | Reaction temperature (° C.) | Reaction time | Yield (%) | Enantio-selectivity (% ee) |
|---|---|---|---|---|---|---|
| 1 | L1 | Sc(OTf)$_3$ | 30 | 72 h | trace | n.d. |
| 2 | L2 | Sc(OTf)$_3$ | 30 | 72 h | trace | n.d |
| 3 | L3 | Sc(OTf)$_3$ | 30 | 72 h | trace | n.d |
| 4 | L4 | Sc(OTf)$_3$ | 30 | 72 h | 9 | 99 |
| 5 | L5 | Sc(OTf)$_3$ | 30 | 72 h | 30 | 99 |
| 6 | L5 | Er(OTf)$_3$ | 30 | 72 h | 87 | 98 |
| 7 | L5 | Ho(OTf)$_3$ | 30 | 72 h | 74 | 97 |
| 8 | L5 | Yb(OTf)$_3$ | 30 | 72 h | 91 | 98 |
| 9 | L5 | Y(OTf)$_3$ | 30 | 72 h | 73 | 98 |
| 10 | L5 | Gd(OTf)$_3$ | 30 | 72 h | 93 | 97 |
| 11 | L6 | Gd(OTf)$_3$ | 30 | 72 h | 99 | 98 |
| 12 | L6 | Gd(OTf)$_3$ | 30 | 72 h | 98 | 98 |
| 13 | L6 | Gd(OTf)$_3$ | 25 | 120 h | 91 | 98 |
| 14 | L6 | Gd(OTf)$_3$ | 30 | 48 h | 82 | 98 |
| 15 | L6 | Gd(OTf)$_3$ | 40 | 24 h | 98 | 98 |
| 16 | L6 | Gd(OTf)$_3$ | 50 | 12 h | 98 | 98 |

(n.d.: not detected)

Example 2: Michael Addition of α,β-Unsaturated pyrazole amide Compound with nitroalkane Compound, Being Catalyzed by chiral amine oxide L6-Gd(OTf)$_3$ Complex Gd(OTf)$_3$ (Nos. 1-16, 20-23, and 25-27: 0.0075 mmol, and Nos. 17-19, and 24: 0.01 mmol), chiral amine oxide L6 (Nos. 1-16, 20-23, and 25-27: 0.009 mmol, and Nos. 17-19, and 24: 0.012 mmol) (where the molar ratio of the chiral amine oxide L6 to gadolinium trifluoromethanesulfonate (Gd(OTf)$_3$) is 1.2:1.0), an α,β-unsaturated amide (0.1 mmol), a 4 Å molecular sieve (Nos. 1-16, and 20-27: 30 mg, No. 18: 100 mg, No. 17 and 19: 60 mg), and a stirrer were added to a reaction vessel. The reaction vessel was purged 3 times with nitrogen, and then dichloromethane (6.2 mmol) and a nitroalkane (0.93 mmol) were added and stirred at 30° C. for 72 hrs. The product was purified by column chromatography, and the enantiomeric excess of the product was determined by chiral HPLC. The reaction formula is shown as below:

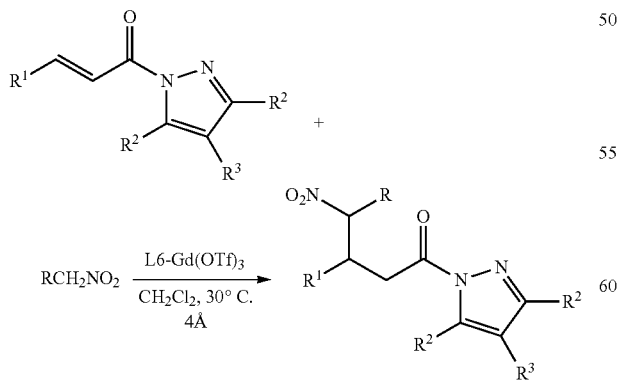

The result is shown in Table 2: (d.r: diastereoselectivity of compounds containing two or more chiral centers)

TABLE 2

Asymmetric Michael addition of α,β-unsaturated pyrazole amide compound with nitroalkane compound, being catalyzed by chiral amine oxide L6-Gd(OTf)$_3$ complex

| No. | R, R1, R2, and R3 | Yield (%) | Enantioselectivity (% ee) |
|---|---|---|---|
| 1 | H, C$_6$H$_5$, CH$_3$, H | 99 | 99 |
| 2 | H, 4-FC$_6$H$_4$, CH$_3$, H | 99 | 99 |
| 3 | H, 4-ClC$_6$H$_4$, CH$_3$, H | 98 | 98 |
| 4 | H, 4-BrC$_6$H$_4$, CH$_3$, H | 96 | 98 |
| 5 | H, 4-MeC$_6$H$_4$, CH$_3$, H | 95 | 99 |
| 6 | H, 4-MeOC$_6$H$_4$, CH$_3$, H | 89 | 99 |
| 7 | H, 3-BrC$_6$H$_4$, CH$_3$, H | 98 | 98 |
| 8 | H, 3-MeC$_6$H$_4$, CH$_3$, H | 96 | 99 |
| 9 | H, 2-BrC$_6$H$_4$, CH$_3$, H | 99 | 99 |
| 10 | H, 2-MeOC$_6$H$_4$, CH$_3$, H | 99 | 99 |
| 11 | H, 3,4-Cl$_2$C$_6$H$_3$, CH$_3$, H | 96 | 99 |
| 12 | H, 3,4-(MeO)$_2$C$_6$H$_3$, CH$_3$, H | 83 | 99 |
| 13 | H, 2-Furyl, CH$_3$, H | 56 | 97 |
| 14 | H, 2-Thienyl, CH$_3$, H | 58 | 98 |
| 15 | H, CH$_3$, CH$_3$, H | 69 | 98 |
| 16 | H, Pr, CH$_3$, H | 87 | 98 |
| 17 | H, Pent, CH$_3$, H | 65 | 98 |
| 18 | H, bu, CH$_3$, H | 77 | 98 |
| 19 | H, EtO, CH$_3$, H | 53 | 95 |
| 20 | H, EtOOC, CH$_3$, H | 67 | 95 |
| 21 | H, 4-ClC$_6$H$_4$, CH$_3$, Cl | 94 | 99 |
| 22 | H, 4-ClC$_6$H$_4$, CH$_3$, Br | 96 | 99 |
| 23 | H, 4-ClC$_6$H$_4$, CH$_3$, I | 97 | 99 |
| 24 | H, 4-ClC$_6$H$_4$, C$_6$H$_5$, H | 39 | 81 |
| 25 | CH$_3$, 4-ClC$_6$H$_4$, CH$_3$, H | 94 | 98/98 (d.r. 1.6/1) |
| 26 | Et, 4-ClC$_6$H$_4$, CH$_3$, H | 87 | 99/98 (d.r. 1.2/1) |
| 27 | PhCH$_2$, 4-ClC$_6$H$_4$, CH$_3$, H | 98 | 99/98 (d.r. 1.1/1) |

Example 3: Asymmetric Michael Addition of α,β-Unsaturated pyrazole amide Compound with nitroalkane Compound, Being Catalyzed by a Complex Formed by chiral amine oxide with Rare Earth Metal A rare earth metal compound (Nos. 1-11: 0.01 mmol, and No. 12-16: 0.0075 mmol), a chiral amine oxide ligand (No. 1-11: 0.012 mmol, and No. 12-16: 0.009 mmol), an α,β-unsaturated pyrazole amide 1a (0.1 mmol), a 4 Å molecular sieve (30 mg) and a stirrer were added to a reaction vessel. The reaction vessel was purged 3 times with nitrogen, and then dichloromethane (6.2 mmol) and nitromethane (Nos. 1-11: 5.6 mmol, and Nos. 12-16: 0.93 mmol) were added and stirred at 25-50° C. for 12-120 hrs. The reaction was detected by TLC. The product was purified by column chromatography, and the enantiomeric excess of the product was determined by HPLC (Daicel chiralcel IE, V$_{n-hexane}$: V$_{isopropanol}$=90:10, flow rate: 1.0 mL/min). The result is shown in Table 3. The reaction formula and the structure of the chiral amine oxide ligand are shown as below:

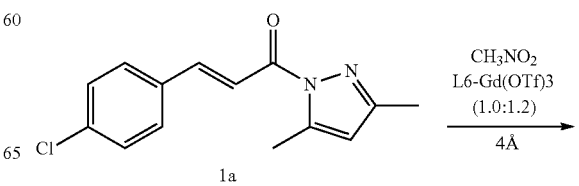

-continued

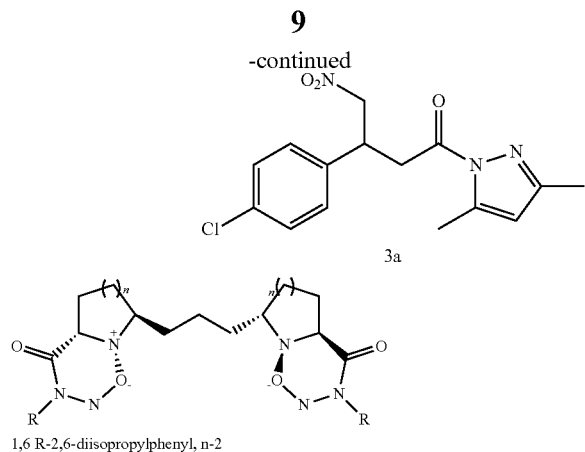

3a 1,6 R-2,6-diisopropylphenyl, n-2

TABLE 3

Asymmetric Michael addition of α,β-unsaturated
pyrazole amide compound with nitroalkane compound, being
catalyzed by chiral amine oxide L6-Gd(OTf)$_3$ complex
in various solvents at various temperatures

| No. | Reaction solvent | Reaction temperature (° C.) | Reaction time | Yield (%) | Enantio-selectivity (% ee) |
|---|---|---|---|---|---|
| 1 | Tetrahydrofuran | 30 | 72 h | 94 | 98 |
| 2 | Methyl t-butyl ether | 30 | 72 h | 92 | 98 |
| 3 | Ethyl acetate | 30 | 72 h | 94 | 97 |
| 4 | Toluene | 30 | 72 h | 97 | 98 |
| 5 | Hexane | 30 | 72 h | 89 | 95 |
| 6 | Tetrahydrofuran | 40 | 72 h | 92 | 98 |
| 7 | Methyl t-butyl ether | 50 | 72 h | 92 | 97 |
| 8 | Ethyl acetate | 50 | 72 h | 92 | 96 |
| 9 | Toluene | 25 | 72 h | 96 | 98 |
| 10 | Hexane | 50 | 12 h | 91 | 95 |

Example 4: Scaled-Up Experiment 1

To a round-bottom flask equipped with a magnetic stirrer, the amine oxide ligand L6 (0.24 mmol), gadolinium trifluoromethanesulfonate (0.2 mmol), the unsaturated amide No. 2 (0.976 g, 4 mmol), and a 4 Å molecular sieve (1.2 g) were added, and purged 3 times with nitrogen. Then dichloromethane (186 mmol) and nitromethane (37.2 mmol) were added and stirred at 30° C. for 96 hrs. After separation by silica gel column chromatography, 1.217 g of a catalytic reaction product as white solid was obtained (Yield: 99%). The enantioselectivity of the product was determined to be 99% ee by HPLC (Daicel chiralcel IE, $V_{n\text{-}hexane}$:$V_{isopropanol}$=90:10, flow rate: 1.0 mL/min).

Example 5: Scaled-Up Experiment 2

To a round-bottom flask equipped with a magnetic stirrer, the amine oxide ligand L6 (0.36 mmol), gadolinium trifluoromethanesulfonate (0.3 mmol), the unsaturated amide No. 3 (1.04 g, 4 mmol), and a 4 Å molecular sieve (1.2 g) were added, and purged 3 times with nitrogen. Then dichloromethane (186 mmol) and nitromethane (37.2 mmol) were added and stirred at 30° C. for 72 hrs. After separation by silica gel column chromatography, 1.278 g of a catalytic reaction product as white solid was obtained (Yield: 99%). The enantioselectivity of the product was determined to be 98% ee by HPLC (Daicel chiralcel IE, $V_{n\text{-}hexane}$:$V_{isopropanol}$=90:10, flow rate: 1.0 mL/min).

Example 6: Scaled-Up Experiment 3

To a round-bottom flask equipped with a magnetic stirrer, the amine oxide ligand L6 (0.72 mmol), gadolinium trifluoromethanesulfonate (0.6 mmol), the unsaturated amide No. 18 (1.236 g, 6 mmol), and a 4 Å molecular sieve (6.5 g) were added, and purged 3 times with nitrogen. Then dichloromethane (325.5 mmol) and nitromethane (55.8 mmol) were added and stirred at 30° C. for 72 hrs. After separation by silica gel column chromatography, 1.34 g of a catalytic reaction product as colorless liquid was obtained (Yield: 83%). The enantioselectivity of the product was determined to be 99% ee by HPLC (Daicel chiralcel IE, $V_{n\text{-}hexane}$:$V_{isopropanol}$=90:10, flow rate: 1.0 mL/min).

Applying γ-nitropyrazole amide Compound in Synthesis

Example 7: Esterification of Catalytic Reaction Product

After the catalytic reaction was complete (where the initial α,β-unsaturated pyrazole amide was 0.1 mmol), DBU (0.067 mmol) and methanol (2.5 mmol) were added to a test tube containing the reaction solution 3a or 3b respectively, and stirred overnight at room temperature. The product was separated and purified by column chromatography, and analyzed by HPLC (3a: Daicel chiralcel IB, $V_{n\text{-}hexane}$:$V_{isopropanol}$=90:10, flow rate: 1.0 mL/min, and 3b: Daicel chiralcel IC, $V_{n\text{-}hexane}$:$V_{isopropanol}$=95:5, flow rate: 0.8 mL/min). The result is shown as below.

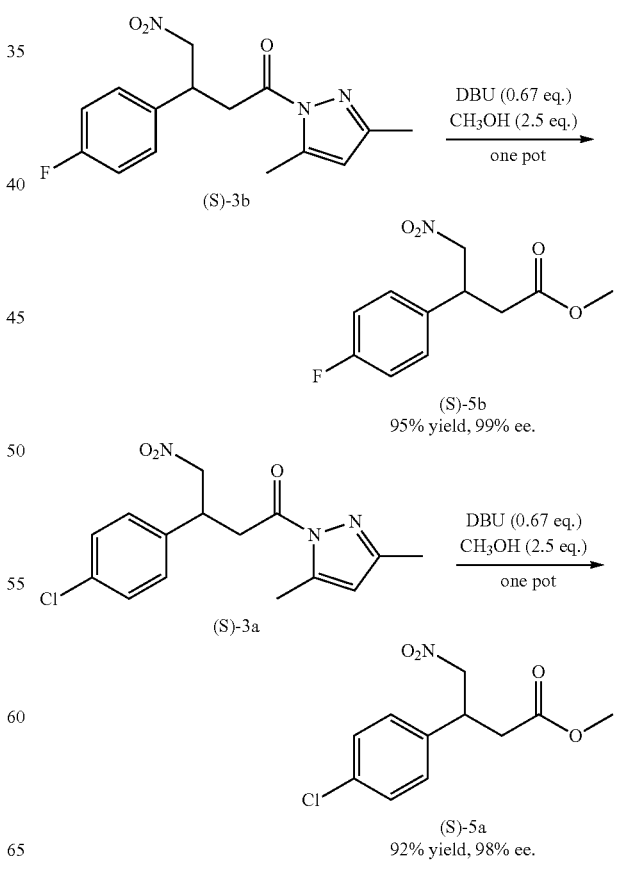

5a and 5b can be used in the synthesis of drug molecules Baclofen and Paroxetine following a method as described in the literature (Org. Lett. 2012, 14, 1516).

After the catalytic reaction was complete (where the initial α,β-unsaturated pyrazole amide was 0.1 mmol), triethylamine (0.067 mmol) and methanol (2.5 mmol) were added to a test tube containing the reaction solution 3b, and stirred overnight at room temperature. The product was separated and purified by column chromatography, and analyzed by HPLC (3a: Daicel chiralcel IB, $V_{n\text{-}hexane}$:$V_{isopropanol}$=90:10, flow rate: 1.0 mL/min, and 3b: Daicel chiralcel IC, $V_{n\text{-}hexane}$:$V_{isopropanol}$=95:5, flow rate: 0.8 mL/min). (S)-5b was obtained (Yield 94.2%, 99% ee).

After the catalytic reaction was complete (where the initial α,β-unsaturated pyrazole amide was 0.1 mmol), dimethylaniline (0.08 mmol) and methanol (2.5 mmol) were added to a test tube containing the reaction solution 3a, and stirred overnight at room temperature. The product was separated and purified by column chromatography, and analyzed by HPLC (3a: Daicel chiralcel IB, $V_{n\text{-}hexane}$:$V_{isopropanol}$=90:10, flow rate: 1.0 mL/min), (3b: Daicel chiralcel IC, $V_{n\text{-}hexane}$:$V_{isopropanol}$=95:5, flow rate: 0.8 mL/min). (S)-5a was obtained (Yield 92%, 98.6% ee).

Because the detection, separation and purification of fatty ester compounds are inconvenient, the esterification process is performed stepwise. 3t (46.2 mg, 0.173 mmol, 98% ee) was added to a reaction vessel, and then dichloromethane (7.8 mmol), DBU (0.1 mmol), and methanol (3.72 mmol) were added in sequence, and stirred for 5 hrs at room temperature. The product was separated and purified by column chromatography, and analyzed by HPLC (Daicel chiralcel IE, $V_{n\text{-}hexane}$:$V_{isopropanol}$=95:5, flow rate: 1.0 mL/min). The yield of the product is 95%, and the enantioselectivity is 98% ee. The result is shown as below.

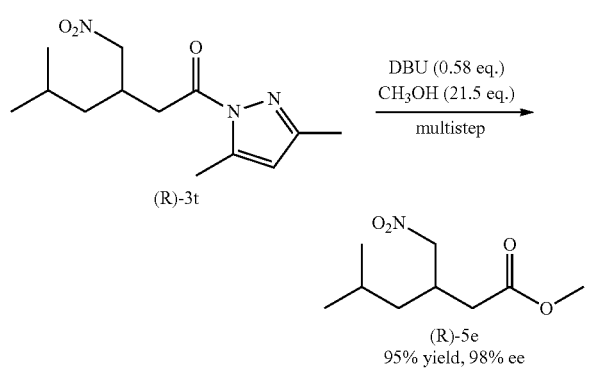

Example 8: Synthesis of pregabalin

Chengdu Organic Chemicals Co., Ltd, Chinese Academy of Sciences discloses a method for converting racemic 5c into racemic 6c. In the method, 5c is subjected to a reductive ring-closing reaction by using Raney nickel-$H_2$ as a hydrogenation reagent, to obtain 6c with a yield of 97%. Despite the good result to some extent, in operation, it is very complex. In addition, some dangerous reagents such as Raney nickel and hydrogen are used during the process (CN 102115449A. 06, 07, 2011).

Herein, a method for synthesizing 6c compound with 5c compound is provided, the reaction condition is mild and the operation is simple, and the reaction is highly efficient.

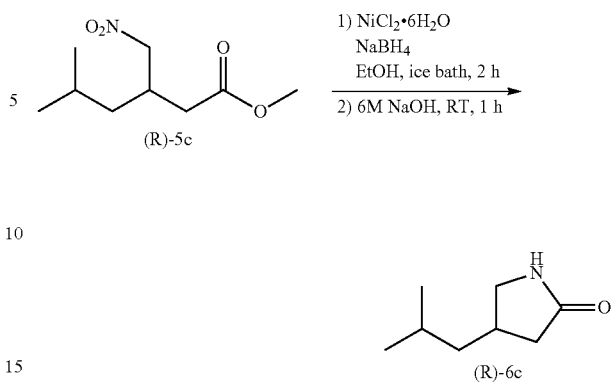

To a round-bottom flask equipped with a magnetic stirrer, 5c (68.82 mg, 0.34 mmol), $NiCl_2.6H_2O$ (80.6 mg, 0.34 mmol), and EtOH (33.9 mmol) were added, and left in an ice bath for 5 min. Then, $NaBH_4$ (140.9 mg, 3.74 mmol) was slowly added, and the reaction solution was continuously stirred in the ice bath for 2 hrs. The reaction was quenched with 1 mL ethanol, and then returned back to room temperature. 1 mL of 6 mol/L sodium hydroxide solution was added to the reaction solution, and continuously stirred for 1 hr. After 1 hr, 2 mol/L hydrochloric acid solution was added to the reaction solution, adjusted to a pH below 7, and extracted with dichloromethane (4×6 mL). The organic layers were combined, dried over anhydrous sodium sulfate, then filtered under suction and rotarily dried, to obtain the product 6c (Yield: 95%). The enantioselectivity of the product was determined to be 97% ee by HPLC (Daicel chiralcel AD-H, $V_{n\text{-}hexane}$:$V_{isopropanol}$=96:4, flow rate: 1.0 mL/min).

As described in the literature (*Tetrahedron*, 2011, 67, 636), after the compound 6c was refluxed for 10 hrs in 6 mol/L hydrochloric acid at 100° C., Pregabalin hydrochloride was obtained with a yield of 95% while ee was maintained.

What is claimed is:

1. An asymmetrically catalyzed synthesis method of a γ-nitropyrazole amide compound, wherein, in the reaction that a nitroalkane and an α,β-unsaturated pyrazole amide are employed as raw materials, a complex formed by a chiral amine oxide with a rare earth metal compound is served as a catalyst, a 4 Å molecular sieve is served as an additive, after the reaction finished, to obtain a γ-nitropyrazole amide compound, wherein, the structure of the nitroalkane is $RCH_2NO_2$, in which R=H, $CH_3$, Et, or Bn;

the structure of the α,β-unsaturated pyrazole amide compound is

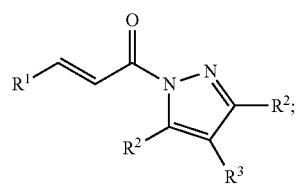

the γ-nitropyrazole amide compound has a structure of:

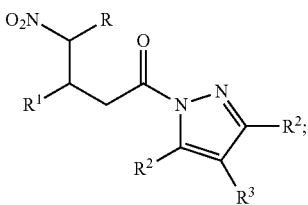

the structure of the chiral amine oxide ligand is

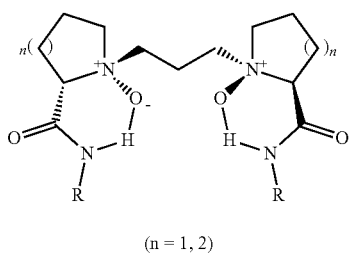

(n = 1, 2)

in which $R^1$=$C_6H_5$, 4-F$C_6H_4$, 4-Cl$C_6H_4$, 4-Br$C_6H_4$, 4-Me$C_6H_4$, 4-MeO$C_6H_4$, 3-Br$C_6H_4$, 3-Me$C_6H_4$, 2-Br$C_6H_4$, 2-MeO$C_6H_4$, 3,4-$Cl_2C_6H_3$, 3,4-(MeO)$_2$$C_6H_3$, 2-Furyl, 2-Thienyl, $CH_3$, Pr, Pent, $^i$Bu, EtO, or EtOOC; and $R^2$=$CH_3$, Ph; $R^3$=H, Cl, Br, or I; and n=1, or 2; and R=Ph-, 2,6-Me$_2$C$_6$H$_3$—, 2,6-Et$_2$C$_6$H$_3$—, 2,6-iPr$_2$C$_6$H$_3$—, or Ph$_2$CH—; and the rare earth metal compound is gadolinium trifluoromethanesulfonate [Gd(OTf)$_3$], scandium trifluoromethanesulfonate [Sc(OTf)$_3$], holmium trifluoromethanesulfonate [Ho(OTf)$_3$], ytterbium trifluoromethanesulfonate [Yb(OTf)$_3$], erbium trifluoromethanesulfonate [Er(OTf)$_3$], or yttrium trifluoromethanesulfonate [Y(OTf)$_3$].

2. The preparation method according to claim 1, wherein, the reaction takes place in a solvent selected from pentane, hexane, dichloroethane, chloroform, toluene, ethylbenzene, cumene, tetrahydrofuran, methyl tert-butyl ether, 2-methyltetrahydrofuran, ethyl acetate and isopropyl acetate.

3. The preparation method according to claim 1, wherein, the reaction temperature is 25-50° C.

4. The preparation method according to claim 1, wherein, the nitroalkane and the α,β-unsaturated pyrazole amide are employed as raw materials, the complex formed by a chiral amine oxide with a rare earth metal compound is served as a catalyst, the 4 Å molecular sieve is served as an additive, after a reaction of 12-120 hrs in the solvent of dichloromethane and at a temperature of 25-50° C. under normal pressure, to obtain the γ-nitropyrazole amide compound.

5. The preparation method according to claim 1 or 4, wherein, the molar ratio of the nitroalkane to the α,β-unsaturated pyrazole amide compound is 1.86:1-55.8:1.

6. The preparation method according to claim 5, wherein, the molar ratio of the nitroalkane to the α,β-unsaturated pyrazole amide compound is 9.3:1.

7. The preparation method according to claim 1 or 4, wherein, the molar ratio of the chiral amine oxide to the rare earth metal compound is 0.8:1.0-1.5:1.0.

8. The preparation method according to claim 7, wherein, the molar ratio of the chiral amine oxide to the rare earth metal compound is 1.2:1.0.

9. The preparation method according to claim 1 or 4, wherein, the amount of the 4 Å molecular sieve is such that 10-100 mg of the 4 Å molecular sieve is needed per 0.1 mmol of the α,β-unsaturated pyrazole amide.

10. The preparation method according to claim 1 or 4, wherein, the rare earth metal compound is gadolinium trifluoromethanesulfonate [Gd(OTf)$_3$].

11. The preparation method according to claim 1 or 4, wherein, in the chiral amine oxide ligand, n=2, and R=2,6-iPr$_2$C$_6$H$_3$—.

12. The preparation method according to claim 1 or 4, wherein, the molar ratio of the α,β-unsaturated pyrazole amide compound to the rare earth metal compound is 20:1-10:1.

13. The preparation method according to claim 1 or 4, wherein, 30-100 mg of the 4 Å molecular sieve is needed per 0.1 mmol of the α,β-unsaturated pyrazole amide compound.

14. The preparation method according to any one of claims 1 to 4, further comprising the step of:
reacting the γ-nitropyrazole amide compound with methanol in the presence of an organic base, to obtain an esterified product the esterified product has a structure of:

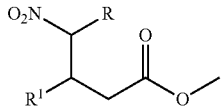

in which R and $R^1$ is as defined in claim 1.

15. The preparation method according to claim 14, wherein, the organic base is selected from the group consisting of triethylamine, diisoproylethylamine, trimethylamine, tri-n-propylamine, tri-n-butylamine, dimethylaniline, diethylaniline, dim ethylbenzylamine, diethylbenzylamine and 1,8-azacyclo[5,4,0]undecene-7.

* * * * *